United States Patent
Hayashi et al.

(10) Patent No.: US 11,492,258 B2
(45) Date of Patent: Nov. 8, 2022

(54) METHOD FOR PRODUCING BIS(FLUOROSULFONYL)AMIDE ALKALI METAL SALT POWDER

(71) Applicant: NIPPON SODA CO., LTD., Tokyo (JP)

(72) Inventors: Kenichi Hayashi, Joetsu (JP); Hiroyuki Nishijima, Takaoka (JP); Masahiro Hori, Takaoka (JP); Toshiaki Nishizawa, Takaoka (JP); Asami Kohori, Takaoka (JP)

(73) Assignee: NIPPON SODA CO., LTD., Tokyo (JP)

( * ) Notice: Subject to any disclaimer, the term of this patent is extended or adjusted under 35 U.S.C. 154(b) by 157 days.

(21) Appl. No.: 16/975,167

(22) PCT Filed: Feb. 26, 2019

(86) PCT No.: PCT/JP2019/007335
§ 371 (c)(1),
(2) Date: Aug. 24, 2020

(87) PCT Pub. No.: WO2019/167949
PCT Pub. Date: Sep. 6, 2019

(65) Prior Publication Data
US 2021/0114877 A1    Apr. 22, 2021

(30) Foreign Application Priority Data
Feb. 28, 2018 (JP) .............................. JP2018-035782

(51) Int. Cl.
*C01B 21/00* (2006.01)
*C01B 21/086* (2006.01)
*B01D 1/22* (2006.01)

(52) U.S. Cl.
CPC ............ *C01B 21/086* (2013.01); *B01D 1/225* (2013.01)

(58) Field of Classification Search
CPC ...... C01B 21/086; B01D 1/221; B01D 1/225; B01D 1/24; B01D 9/0031; B01D 9/0036;
(Continued)

(56) References Cited

U.S. PATENT DOCUMENTS

2003/0190271 A1   10/2003   Noda et al.
2005/0211956 A1   9/2005   Kono et al.
(Continued)

FOREIGN PATENT DOCUMENTS

JP   2005-232415 A   9/2005
JP   2006-043597 A   2/2006
(Continued)

OTHER PUBLICATIONS

Apr. 9, 2019 Search Report issued in International Patent Application No. PCT/JP2019/007335.
(Continued)

*Primary Examiner* — Prem C Singh
*Assistant Examiner* — Brandi M Doyle
(74) *Attorney, Agent, or Firm* — Oliff PLC

(57) ABSTRACT

An object of the present invention is to provide a method for producing a bis(fluorosulfonyl)amide alkali metal salt powder having high purity while suppressing reduction in yield due to thermal decomposition, etc. The method for producing a bis(fluorosulfonyl)amide alkali metal salt powder according to the present invention comprises precipitating a bis(fluorosulfonyl)amide alkali metal salt by conducting distillation using a thin-film evaporator while adding a poor solvent for the bis(fluorosulfonyl)amide alkali metal salt such as an aromatic hydrocarbon solvent and a linear or branched aliphatic hydrocarbon solvent to a solution formed by dissolving the bis(fluorosulfonyl)amide alkali metal salt in a good solvent for the bis(fluorosulfonyl)amide alkali metal salt such as an ester solvent and nitrile solvent.

8 Claims, 1 Drawing Sheet

(58) Field of Classification Search
CPC .... B01D 9/0045; B01D 9/0054; C07C 311/48
See application file for complete search history.

(56) References Cited

U.S. PATENT DOCUMENTS

| | | |
|---|---|---|
| 2013/0068991 A1 | 3/2013 | Sato et al. |
| 2016/0289074 A1 | 10/2016 | Tsubokura et al. |
| 2017/0133715 A1* | 5/2017 | Sato .................... H01M 10/052 |
| 2018/0015386 A1 | 1/2018 | Mukaida et al. |

FOREIGN PATENT DOCUMENTS

| | | |
|---|---|---|
| JP | 2014-201453 A | 10/2014 |
| JP | 2017-052689 A | 3/2017 |
| TW | 201226413 A | 7/2012 |
| WO | 2002/026374 A1 | 4/2002 |
| WO | 2011/149095 A1 | 12/2011 |
| WO | 2016/143776 A1 | 9/2016 |

OTHER PUBLICATIONS

Nov. 4, 2021 Extended Search Report issued in European Patent Application No. 19761157.7.

\* cited by examiner

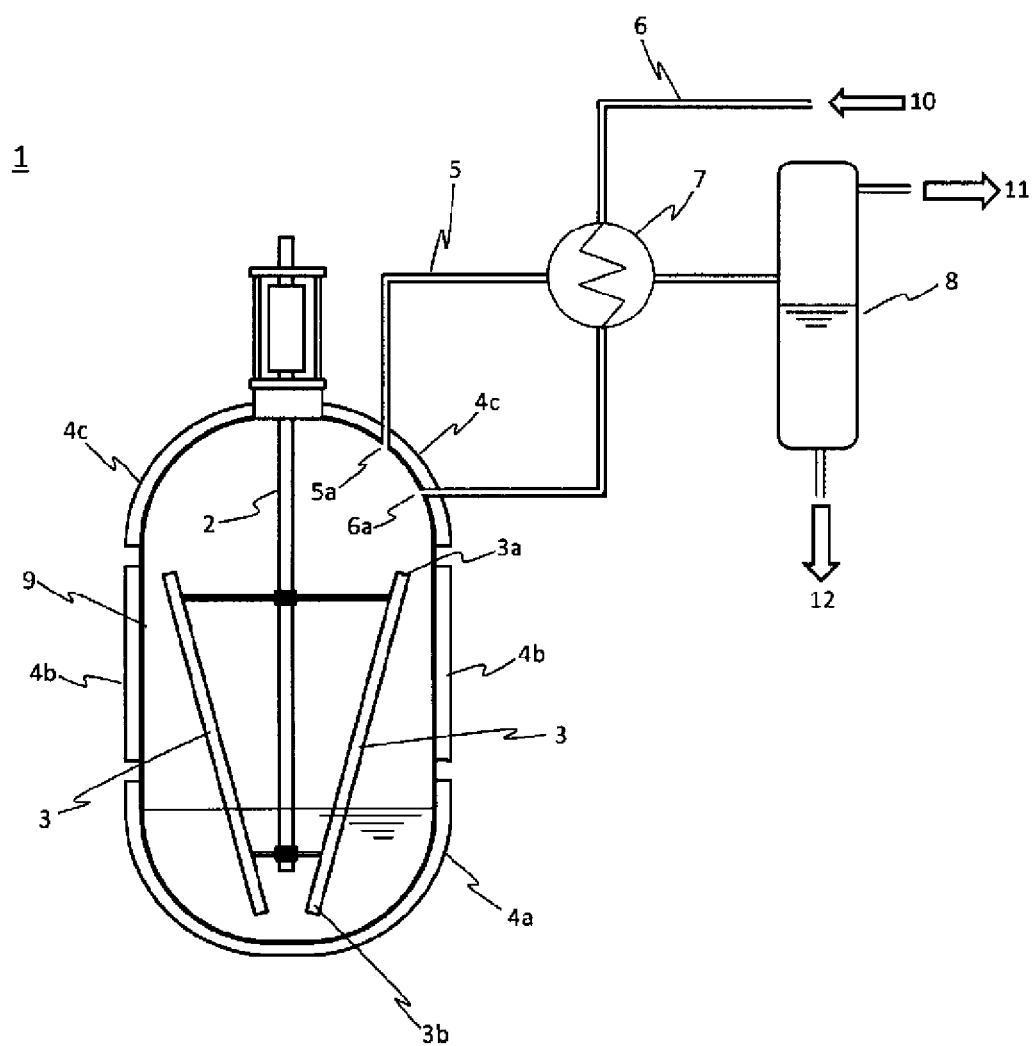

METHOD FOR PRODUCING BIS(FLUOROSULFONYL)AMIDE ALKALI METAL SALT POWDER

TECHNICAL FIELD

The present invention relates to a method for producing a bis(fluorosulfonyl)amide alkali metal salt powder. More specifically, the present invention relates to a method for producing a bis(fluorosulfonyl)amide alkali metal salt powder having high purity while suppressing reduction in yield due to thermal decomposition, etc. The present application claims priority to Japanese Patent No. 2018-35782 filed on Feb. 28, 2018, the content of which is hereby incorporated.

BACKGROUND ART

Patent Document 1 describes that a fluorosulfonyl imide alkali metal salt may be produced by the method described in Patent document 1. Since a fluorosulfonyl imide alkali metal salt does not have high heat resistance, the yield may be reduced when it is heated over a long term. Therefore, Patent document 1 discloses a method for producing a fluorosulfonyl imide alkali metal salt wherein the method comprises a step of concentrating a solution of fluorosulfonyl imide alkali metal salt by distilling off a reaction solvent in the presence of both a reaction solvent and at least one poor solvent for the fluorosulfonyl imide alkali metal salt selected from a group consisting of an aromatic hydrocarbon solvent, an aliphatic hydrocarbon solvent and an aromatic ether solvent, after synthesizing the fluorosulfonyl imide alkali metal salt in the presence of the reaction solvent comprising at least one solvent selected from a group consisting of a carbonate solvent, an aliphatic ether solvent, an ester solvent, an amide solvent, a nitro solvent, a sulfur solvent and a nitrile solvent. Patent document 1 describes that a rotary evaporator, a flask, a vessel type reactor, etc. are used in the concentration step, and that the reaction solvent may be previously removed using a thin-film evaporator or the like before the concentration step in the coexistence of the poor solvent.

PRIOR ART DOCUMENTS

Patent Documents

Patent document 1: Japanese unexamined Patent Application Publication No. 2014-201453

SUMMARY OF THE INVENTION

Object to be Solved by the Invention

An object of the present invention is to provide a method for producing a bis(fluorosulfonyl)amide alkali metal salt powder having high purity while suppressing reduction in yield due to thermal decomposition, etc.

Means to Solve the Object

The present inventors made studies to solve the above object, and consequently completed the present invention encompassing the embodiments below.

[1] A method for producing a bis(fluorosulfonyl)amide alkali metal salt powder comprising precipitating a bis(fluorosulfonyl)amide alkali metal salt by conducting distillation using a thin-film evaporator while adding a poor solvent to a solution formed by dissolving the bis(fluorosulfonyl)amide alkali metal salt in a good solvent.

[2] The method according to [1], wherein
the good solvent is a carbonate solvent, an aliphatic ether solvent, an ester solvent, an amide solvent, a nitro solvent, a sulfur solvent or a nitrile solvent, and
the poor solvent is an aromatic hydrocarbon solvent, a linear or branched aliphatic hydrocarbon solvent, an alicyclic hydrocarbon solvent or an aromatic ether solvent.

[3] The method according to [1] or [2], wherein an equilibrium vapor pressure of the good solvent is higher than an equilibrium vapor pressure of the poor solvent at a temperature for conducting the distillation using the thin-film evaporator.

[4] The method according to any one of [1] to [3], wherein
the thin-film evaporator comprises a vessel having a poor solvent feed inlet and a vapor outlet, a stirring apparatus installed inside the vessel and a heating apparatus for regulating a temperature of a wall surface of the vessel,
the stirring apparatus comprises a vertical rotation axis and a rotor blade capable of pumping up a liquid accumulated on a bottom part of the vessel by a centrifugal force and squirting the pumped-up liquid on an upper part of the wall inside the vessel, and
the squirted liquid naturally flows down along the wall inside the vessel, during which evaporation of the liquid is caused.

Effect of the Invention

According to the method of the present invention, a bis(fluorosulfonyl)amide alkali metal salt powder having high purity may be produced in a short time while suppressing reduction in yield due to thermal decomposition, etc.

When a good solvent solution of a bis(fluorosulfonyl)amide alkali metal salt is simply concentrated, only the viscosity increases and the precipitation is unlikely to occur, and thus the yield of the bis(fluorosulfonyl)amide alkali metal salt powder is lower. It is considered that the reason for this is that there exists some interaction between the bis(fluorosulfonyl)amide alkali metal salt and the good solvent and the bis(fluorosulfonyl)amide alkali metal salt does not separate from the solvent.

BRIEF DESCRIPTION OF DRAWINGS

FIG. 1 is a drawing showing an example of the thin-film evaporator used in the present invention.

MODE OF CARRYING OUT THE INVENTION

The method for producing a bis(fluorosulfonyl)amide alkali metal salt powder according to the present invention comprises precipitating a bis(fluorosulfonyl)amide alkali metal salt by conducting distillation using a thin-film evaporator while adding a poor solvent for the bis(fluorosulfonyl)amide alkali metal salt to a solution formed by dissolving the bis(fluorosulfonyl)amide alkali metal salt in a good solvent for the bis(fluorosulfonyl)amide alkali metal salt.

The bis(fluorosulfonyl)amide alkali metal salt used in the present invention is, for example, a known substance of formula (I).

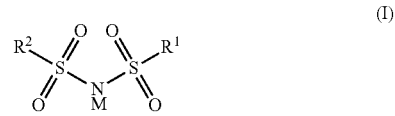

(in formula (I), M is an alkali metal, $R^1$ and $R^2$ are each independently a fluorine atom or a hydrocarbon group having 1 to 6 carbon atoms substituted with at least one fluorine atom.)

As specific examples of a bis(fluorosulfonyl)amide alkali metal salt, bis(fluorosulfonyl)amide lithium salt, bis(perfluoromethylsulfonyl)amide lithium salt, bis(fluorosulfonyl)amide potassium salt, bis(perfluoromethylsulfonyl)amide potassium salt, bis(fluorosulfonyl)amide sodium salt, bis(perfluoromethylsulfonyl)amide sodium salt or the like may be exemplified.

A good solvent is not particularly limited as long as it may dissolve a bis(fluorosulfonyl)amide alkali metal salt in a specified amount or more at room temperature. As a good solvent used preferably in the present invention, a carbonate solvent, an aliphatic ether solvent, an ester solvent, an amide solvent, a nitro solvent, a sulfur solvent and a nitrile solvent may be exemplified. Among these, an aliphatic ether solvent, an ester solvent and a nitrile solvent are preferable. Good solvents may be used alone or used by combination of two or more.

On the other hand, a poor solvent is a solvent not capable of dissolve the bis(fluorosulfonyl)amide alkali metal salt in a specified amount or more at room temperature. As a poor solvent used preferably in the present invention, an aromatic hydrocarbon solvent, a linear or branched aliphatic hydrocarbon solvent, an alicyclic hydrocarbon solvent and an aromatic ether solvent may be exemplified. Among these, an aromatic hydrocarbon solvent and a linear or branched aliphatic hydrocarbon solvent are preferable. As an aromatic hydrocarbon solvent and a linear or branched aliphatic hydrocarbon solvent, a substituted or unsubstituted aromatic hydrocarbon; a substituted or unsubstituted linear aliphatic hydrocarbon, a substituted or unsubstituted branched aliphatic hydrocarbon or the like may be exemplified. Poor solvents may be used alone or used by combination of two or more. A poor solvent to be added may be a solvent which has not been used for the distillation of the present invention, or may be a solvent obtained by condensing and refluxing the vapor exhausted during the distillation of the present invention, or may be a solvent obtained by refining and regenerating the vapor exhausted during the distillation of the present invention.

As for a good solvent and a poor solvent used in the present invention, an equilibrium vapor pressure of the good solvent is preferably higher than an equilibrium vapor pressure of the poor solvent at a temperature for conducting the distillation using the thin-film evaporator. When the poor solvent and the good solvent satisfying such relationship are selected, the good solvent tends to be exhausted through a vapor outlet to the outside of the thin-film evaporator, and the poor solvent tends to remain inside the thin-film evaporator. The temperature of the vapor outlet of the thin-film evaporator is preferably 20 to 90° C. and more preferably 30 to 80° C.

Furthermore, as for a good solvent and a poor solvent used in the present invention, at a pressure for conducting the distillation using the thin-film evaporator, a boiling point of the good solvent is preferably lower than a boiling point of the poor solvent. The difference between the boiling point of the good solvent and the boiling point of the poor solvent at 1 atm is preferably 10° C. or more, more preferably 20° C. or more, further preferably 35° C. or more and even further preferably 45° C. or more.

The maximum temperature for conducting the distillation using a thin-film evaporator is preferably lower than a temperature at which thermal decomposition of a bis(fluorosulfonyl)amide alkali metal salt does not proceed. The temperature of the liquid inside the thin-film evaporator is preferably 25 to 90° C. and more preferably 35 to 80° C. In order to accelerate the evaporation at a lower temperature, it is preferable to conduct the distillation under reduced pressure. In order to prevent entrainment and bumping, the temperature of the liquid inside the thin-film evaporator is preferably lower than the boiling point of the mixture of the good solvent and the poor solvent.

Temperature regulation of the thin-film evaporator may be conducted using a known heating apparatus such as a jacket.

A thin-film evaporator is an apparatus which evaporates a liquid by thinly spreading the liquid into the form of a film and heating the obtained thin film. As a method for the thinly spreading liquid into the form of a film, methods of wiper-type, scraper-type, flow-down liquid-type, centrifugal-type or the like may be exemplified. Among these, methods in which an apparatus for film forming are comprised inside a vessel, such as wiper-type, scraper-type and centrifugal jet-type, are preferable. As a commercially available thin-film evaporator, for example, "short path distiller" (manufactured by UIC GmbH), "WIPRENE®", "EXEVA®" (all manufactured by Kobelco Eco-Solution Co., Ltd.), "Kontro", "Pitched Blade Kontro", "Sevcon®" (all manufactured by Hitachi Plant Technologies, Ltd.), "Hi-Evaolator®" (manufactured by SAKURA SEISAKUSYO, LTD.), "thin-film distiller", "Viscon", "Filmtruder" (all manufactured by KIMURA CHEMICAL PLANTS CO., LTD.), "Hi-U Brusher", "EVA reactor", "Recovery" (all manufactured by Kansai Chemical Engineering Co., Ltd.), "NRH" (manufactured by Nitinan Engineering Co., Ltd.), "EVAPOR®" (manufactured by OKAWARA MFG. CO., LTD.) or the like may be exemplified.

Thin-film evaporator 1 used preferably in the present invention comprises vessel 9 having poor solvent feed inlet 6a and vapor outlet 5a, a stirring apparatus installed inside the vessel, and heating apparatus 4a (lower jacket), 4b (middle jacket) and 4c (upper jacket) for regulating a temperature of a wall surface of the vessel. The stirring apparatus comprises vertical rotation axis 2 and rotor blade 3 capable of pumping up a liquid accumulated on the bottom part of the vessel by a centrifugal force and squirting the pumped-up liquid on the upper part of the wall inside the vessel, and the squirted liquid naturally flows down along the wall inside the vessel, during which the evaporation of the liquid is caused. The rotor blade 3 preferably has pipes or half pipes attached to the vertical rotation axis, for example, as shown in FIG. 1, so that distal ends 3a of the pipes or half pipes are higher than proximal ends 3b of the pipes or half pipes are inclined relative to horizontal plane. When the proximal ends 3b of the pipes or half pipes are in the liquid accumulated on the bottom of the vessel and a rotation speed of the rotor blade reaches a specified rotation speed, the liquid rises inside the pipes or half pipes due to centrifugal force and is squirted from the distal ends 3a. The squirted liquid is sprayed on the upper part of the wall inside the vessel, and the sprayed liquid naturally flows down along the wall. When the depth of the liquid in the vessel is deep, etc., a common stirring blade, for example, a paddle blade, a propeller blade, a ribbon blade, a turbine blade, an edged turbine blade, an anchor blade or the like may be installed under the rotor blade 3 in order to stir the liquid, though not being installed in the thin-film evaporator shown in FIG. 1. The stirring blade installed under the rotor blade 3 may share the vertical rotation axis 2.

The poor solvent to be added is preferably heated to a temperature close to that of the liquid inside the vessel. A method of the heating is not particularly limited, but for example, in heat exchanger (condenser) 7 as shown in FIG. 1, heat exchange between the poor solvent 10 to be added and vapor of the solvent evaporated from the vessel 9 may be conducted to heat the poor solvent 10 and condense a part of the vapor. Condensate 12 obtained by condensation of a part of the vapor and the rest of vapor 11 may be exhausted to the outside of the system without any treatment. When the poor solvent has a higher boiling point than that of the good solvent and most of the good solvent are exhausted in the form of vapor and the vapor temperature is regulated to a temperature at which most of the poor solvent condenses using the heat exchanger 7, the condensate 12 is rich in the poor solvent and the vapor 11 is rich in the good solvent. The condensate rich in the poor solvent is accumulated on the bottom of gas-liquid separator 8. When a density of the poor solvent is higher than the density of the good solvent, the lower layer of the liquid accumulated on the bottom of the gas-liquid separator 8 is rich in the poor solvent. The thus obtained liquid rich in the poor solvent may be returned to the vessel 9. The vapor rich in the good solvent may be exhausted to the outside of the system. The exhausted vapor may be refined by a known method and recycled as a good solvent or a poor solvent. Inside the vessel, reduced pressure is preferable in order to accelerate the evaporation at low temperature. In the thin-film evaporator having the structure shown in FIG. 1, liquid containing seed crystals circulates along the wall, and thus a precipitate is easily grown to an enough size to be easily subjected to solid-liquid separation. Furthermore, since the liquid is sprayed on the upper part of the wall inside the vessel by the rotor blade 3 having the above structure, the efficiency of heat transfer is extremely high and the required time until the completion of precipitation may be reduced.

The addition of the poor solvent may be conducted before the start of the distillation. When the poor solvent is added before the start of the distillation, a part of a bis(fluorosulfonyl)amide alkali metal salt may precipitate, and seed crystals may be generated. These seed crystals may accelerate the precipitation in the distillation stage, grow the precipitate and increase the size thereof. A larger precipitate is more easily subjected to solid-liquid separation. When the amount of generated seed crystals is small, previously prepared seed crystals may be added before the start of the distillation or during the distillation.

The speed of the addition of the poor solvent during the distillation is not particularly limited. The addition of the poor solvent is preferably conducted so that the amount of the liquid in the thin-film evaporator is maintained almost constant. By conducting the addition so that the amount of the liquid is maintained almost constant, the speed of precipitation may be increased while preventing overheating.

The total amount of the poor solvent to be added during the distillation is preferably 100 parts by mass to 10000 parts by mass, more preferably 200 parts by mass to 1000 parts by mass and further preferably 300 parts by mass to 800 parts by mass with respect to 100 parts by mass of the good solvent. The total amount of the poor solvent to be added during the distillation includes the amount of the poor solvent contained in the condensate returned to the vessel.

After a bis(fluorosulfonyl)amide alkali metal salt is precipitated by distillation as above, the temperature of the liquid inside the vessel is decreased, then solid-liquid separation is conducted. Then, the remaining solvent is evaporated and removed from the precipitate collected in solid-liquid separation. Thus, the bis(fluorosulfonyl)amide alkali metal salt powder having high purity may be obtained. Solid-liquid separation may be conducted by, for example, a centrifugation method, a decantation method, a filtration method or the like. Removal of solvent may be conducted by a known drying method, for example, a method of the drying under reduced pressure, a vacuum drying method, a drying method under normal pressure or the like.

EXAMPLES

Next, the present invention will be described more specifically by showing Examples. However, the technical scope of the present invention is not limited to the Examples.

Example 1

A solution of 56.26 g of bis(fluorosulfonyl)amide lithium salt (LiFSI) and 56.29 g of isopropyl acetate (boiling point 89° C., density 0.88 g/cm$^3$), and 30.03 g of decane (boiling point 174.2° C., density 0.7 g/cm$^3$) were added to a 1-L cylindrical round-bottom separable flask made of glass and having a diameter of 11 cm, and the flask was covered with a four-neck separable cover. To this, a stirring apparatus having a rotor blade (distance between distal ends 10 cm, distance between proximal ends 5 cm, height 9 cm) consisting of a vertical rotation axis and two half pipes having a width of 2 cm as shown in FIG. 1 was attached. Furthermore, a dropping funnel filled with decane (poor solvent), a condenser and a thermometer were attached to specified places.

The separable flask was soaked in a hot water bath at 60° C. to a level immediately below a flange. The degree of reduced pressure was adjusted so that the temperature of the condenser inlet of 48° C. was obtained while rotating the rotor blade at 350 rpm, and the distillation was started. The liquid accumulated on the bottom of the separable flask rose inside the half pipes due to centrifugal force, squirted from the distal ends and sprayed on the wall of a level immediately below the flange of the separable flask. The sprayed liquid flowed down along the wall. While decane was added dropwise to the flask so that the amount of the liquid in the separable flask was maintained constant, and while the rotor blade was rotated, the distillation was continued. At the time when the dropwise addition of 449.57 g of decane was completed (about 74 minutes from the start of the dropwise addition), the rotor blade was stopped and the pressure was returned to normal pressure.

The liquid in the separable flask was cooled to room temperature and filtrated to collect a precipitate. The collected precipitate was washed with methylene chloride and dried under reduced pressure. 49.86 g of LiFSI (yield 88.6%) was obtained.

Comparative Example 1

A solution of 56.71 g of bis(fluorosulfonyl)amide lithium salt (LiFSI) and 56.77 g of isopropyl acetate, and 30.98 g of decane were added to a 1-L cylindrical round-bottom separable flask made of glass and having a diameter of 11 cm, and the flask was covered with a four-neck separable cover. To this, a stirring apparatus having a vertical rotation axis and a semi-circle stirring blade (width 7.5 cm, thickness 4 mm, height 2 cm) was attached. Furthermore, a dropping funnel filled with decane (poor solvent), a condenser and a thermometer were attached to specified places.

The separable flask was soaked in a hot water bath at 60° C. to a level immediately below a flange. The degree of reduced pressure was adjusted so that the temperature of the condenser inlet of 48° C. was obtained while rotating the semi-circle stirring blade at 350 rpm, and the distillation was started. As for the liquid inside the separable flask, the height of the liquid in contact with the wall of the separable flask slightly rose due to centrifugal force relative to the case of still-standing. While decane was added dropwise to the flask so that the amount of the liquid in the separable flask was maintained constant, and while the stirring blade was rotated, the distillation was continued. At the time when the dropwise addition of 567.64 g of decane was completed (about 76 minutes from the start of the dropwise addition), the stirring blade was stopped and the pressure was returned to normal pressure.

The liquid in the separable flask was cooled to room temperature and filtrated to collect a precipitate. The collected precipitate was washed with methylene chloride and dried under reduced pressure. 35.86 g of LiFSI (yield 63.2%) was obtained.

Example 2

A solution of 56.43 g of bis(fluorosulfonyl)amide lithium salt (LiFSI) and 56.42 g of acetonitrile (boiling point 82° C., density 0.786 g/cm$^3$), and 30.01 g of toluene (boiling point 110.63° C., density 0.867 g/cm$^3$) were added to a 1-L cylindrical round-bottom separable flask made of glass and having a diameter of 11 cm, and the flask was covered with a four-neck separable cover. To this, a stirring apparatus having a rotor blade (distance between distal ends 10 cm, distance between proximal ends 5 cm, height 9 cm) consisting of a vertical rotation axis and two half pipes having a width of 2 cm as shown in FIG. 1 was attached. Furthermore, a dropping funnel filled with toluene (poor solvent), a condenser and a thermometer were attached to specified places.

The separable flask was soaked in a hot water bath at 60° C. to a level immediately below a flange. The degree of reduced pressure was adjusted so that the temperature of the condenser inlet of 49° C. was obtained while rotating the rotor blade at 350 rpm, and the distillation was started. The liquid accumulated on the bottom of the separable flask rose inside the half pipes due to centrifugal force, squirted from the distal ends and sprayed on the wall of a level immediately below the flange of the separable flask. The sprayed liquid flowed down along the wall. While toluene was added dropwise to the flask so that the amount of the liquid in the separable flask was maintained constant, and while the rotor blade was rotated, the distillation was continued. At the time when the dropwise addition of 736.36 g of toluene was completed (about 73 minutes from the start of the dropwise addition), the pressure was returned to normal pressure.

The liquid in the separable flask was cooled to room temperature and filtrated to collect a precipitate. The collected precipitate was washed with methylene chloride and dried under reduced pressure. 52.34 g of LiFSI (yield 92.8%) was obtained.

Comparative Example 2

A solution of 56.26 g of bis(fluorosulfonyl)amide lithium salt (LiFSI) and 56.32 g of acetonitrile, and 30.00 g of toluene were added to a 1-L cylindrical round-bottom separable flask made of glass and having a diameter of 11 cm, and the flask was covered with a four-neck separable cover. To this, a stirring apparatus having a vertical rotation axis and a semi-circle stirring blade (width 7.5 cm, thickness 4 mm, height 2 cm) was attached. Furthermore, a dropping funnel filled with toluene (poor solvent), a condenser and a thermometer were attached to specified places.

The separable flask was soaked in a hot water bath at 60° C. to a level immediately below a flange. The degree of reduced pressure was adjusted so that the temperature of the condenser inlet of 49° C. was obtained while rotating the semi-circle stirring blade at 350 rpm, and the distillation was started. The height of the liquid in contact with the wall of the separable flask slightly rose due to centrifugal force relative to the case of still-standing. While toluene was added dropwise to the flask so that the amount of the liquid in the separable flask was maintained constant, and while the stirring blade was rotated, the distillation was continued. At the time when the dropwise addition of 732.46 g of toluene was completed (about 104 minutes from the start of the dropwise addition), the stirring blade was stopped and the pressure was returned to normal pressure.

The liquid in the separable flask was cooled to room temperature and filtrated to collect a precipitate. The collected precipitate was washed with methylene chloride and dried under reduced pressure. 46.10 g of LiFSI (yield 81.9%) was obtained.

EXPLANATION OF LETTERS OR NUMERALS

1: thin-film evaporator
2: rotation axis
3: rotor blade (pipe or half pipe)
4a: lower jacket
4b: middle jacket
4c: upper jacket
5: vapor exhaust pipe
5a: vapor outlet
6: poor solvent feed pipe
6a: poor solvent feed inlet
7: heat exchanger (condenser)
8: gas-liquid separator
9: vessel
10: poor solvent
11: vapor
12: condensate

The invention claimed is:

1. A method for producing a bis(fluorosulfonyl)amide alkali metal salt powder comprising precipitating a bis(fluorosulfonyl)amide alkali metal salt by conducting distillation using a thin-film evaporator while adding a poor solvent to a solution formed by dissolving the bis(fluorosulfonyl)amide alkali metal salt in a good solvent,
wherein previously prepared seed crystals are added before the start of the distillation or during the distillation.

2. The method according to claim 1, wherein
the good solvent is a carbonate solvent, an aliphatic ether solvent, an ester solvent, an amide solvent, a nitro solvent, a sulfur solvent or a nitrile solvent, and
the poor solvent is an aromatic hydrocarbon solvent, a linear or branched aliphatic hydrocarbon solvent, an alicyclic hydrocarbon solvent or an aromatic ether solvent.

3. The method according to claim 1, wherein an equilibrium vapor pressure of the good solvent is higher than an equilibrium vapor pressure of the poor solvent at a temperature for conducting the distillation using the thin-film evaporator.

4. The method according to claim 1, wherein the thin-film evaporator comprises a vessel having a poor solvent feed inlet and a vapor outlet, a stirring apparatus installed inside the vessel and a heating apparatus for regulating a temperature of a wall surface of the vessel, the stirring apparatus comprises a vertical rotation axis and a rotor blade capable of pumping up a liquid accumulated on a bottom part of the vessel by a centrifugal force and squirting the pumped-up liquid on an upper part of the wall inside the vessel, and the squirted liquid naturally flows down along the wall inside the vessel, during which evaporation of the liquid is caused.

5. The method according to claim 2, wherein an equilibrium vapor pressure of the good solvent is higher than an equilibrium vapor pressure of the poor solvent at a temperature for conducting the distillation using the thin-film evaporator.

6. The method according to claim 2, wherein the thin-film evaporator comprises a vessel having a poor solvent feed inlet and a vapor outlet, a stirring apparatus installed inside the vessel and a heating apparatus for regulating a temperature of a wall surface of the vessel, the stirring apparatus comprises a vertical rotation axis and a rotor blade capable of pumping up a liquid accumulated on a bottom part of the vessel by a centrifugal force and squirting the pumped-up liquid on an upper part of the wall inside the vessel, and the squirted liquid naturally flows down along the wall inside the vessel, during which evaporation of the liquid is caused.

7. The method according to claim 3, wherein the thin-film evaporator comprises a vessel having a poor solvent feed inlet and a vapor outlet, a stirring apparatus installed inside the vessel and a heating apparatus for regulating a temperature of a wall surface of the vessel, the stirring apparatus comprises a vertical rotation axis and a rotor blade capable of pumping up a liquid accumulated on a bottom part of the vessel by a centrifugal force and squirting the pumped-up liquid on an upper part of the wall inside the vessel, and the squirted liquid naturally flows down along the wall inside the vessel, during which evaporation of the liquid is caused.

8. The method according to claim 5, wherein the thin-film evaporator comprises a vessel having a poor solvent feed inlet and a vapor outlet, a stirring apparatus installed inside the vessel and a heating apparatus for regulating a temperature of a wall surface of the vessel, the stirring apparatus comprises a vertical rotation axis and a rotor blade capable of pumping up a liquid accumulated on a bottom part of the vessel by a centrifugal force and squirting the pumped-up liquid on an upper part of the wall inside the vessel, and the squirted liquid naturally flows down along the wall inside the vessel, during which evaporation of the liquid is caused.

* * * * *